United States Patent [19]

Persson

[11] Patent Number: 4,868,769
[45] Date of Patent: Sep. 19, 1989

[54] METHOD AND AN APPARATUS FOR DETERMINATION OF BASIC VALUES

[75] Inventor: Sture Persson, Skellefteå, Sweden

[73] Assignee: Skega AB, Ersmark, Sweden

[21] Appl. No.: 14,712

[22] Filed: Feb. 13, 1987

[30] Foreign Application Priority Data

Feb. 13, 1986 [SE] Sweden .................. 8600642

[51] Int. Cl.[4] ............... G01R 27/26; B29C 35/00; G06F 15/46
[52] U.S. Cl. .................... 364/550; 264/40.1; 425/40; 73/146; 324/61 R; 364/473; 364/500
[58] Field of Search ............. 364/138, 473, 500, 550; 374/47; 340/870.37, 870.38, 870.17; 264/22, 27, 40.1, 40.2; 425/143, 28.1, 40, 41; 73/118, 117.2, 146; 324/61 R, 61 P

[56] References Cited

U.S. PATENT DOCUMENTS

| | | | |
|---|---|---|---|
| 3,039,297 | 6/1962 | Peter et al. | 374/47 |
| 3,628,004 | 12/1971 | Claxton et al. | 364/473 X |
| 3,791,792 | 2/1974 | Lindsay | 264/40.2 X |
| 3,819,915 | 6/1974 | Smith | 364/473 |
| 4,044,600 | 8/1977 | Claxton et al. | 364/474 X |
| 4,301,858 | 11/1981 | Mock | 340/870.37 X |
| 4,344,142 | 8/1982 | Diehr et al. | 364/473 |
| 4,510,103 | 4/1985 | Yamaguchi et al. | 264/40.2 |
| 4,514,812 | 4/1985 | Miller et al. | 364/473 |
| 4,546,438 | 10/1985 | Prewitt et al. | 364/474 |
| 4,748,400 | 5/1988 | Typpo | 324/61 R |

FOREIGN PATENT DOCUMENTS 85012706 10/1988 Sweden .

OTHER PUBLICATIONS

"Cure Meters and Their Problems", R. H. Norman-pp. 246-256.
"Vulkanisationssysteme", E. R. Rodger-pp. 124-128, 300-312 (no translation).

Primary Examiner—Parshotam S. Lall
Assistant Examiner—Joseph L. Dixon
Attorney, Agent, or Firm—Cushman, Darby & Cushman

[57] ABSTRACT

A method and an apparatus for determination of basic values from a material specimen to analyze the vulcanization characteristic of the material and to enable measuring of a vulcanization process during the vulcanization in a rapid and safe manner. According to the method the specimen is shaped with resulting true measured values under pressure and at a temperature preferably in excess of 100° C. to a predetermined form and thickness between two electrodes with plane-parallel sides facing each other which during the shaping process are brought into an intimate contact with the shaped body to form together a capacitor, the capacitance and loss angle of this capacitor being measured and recorded together and simultaneously with the temperature of at least one of the two electrodes as the basic values.

12 Claims, 22 Drawing Sheets

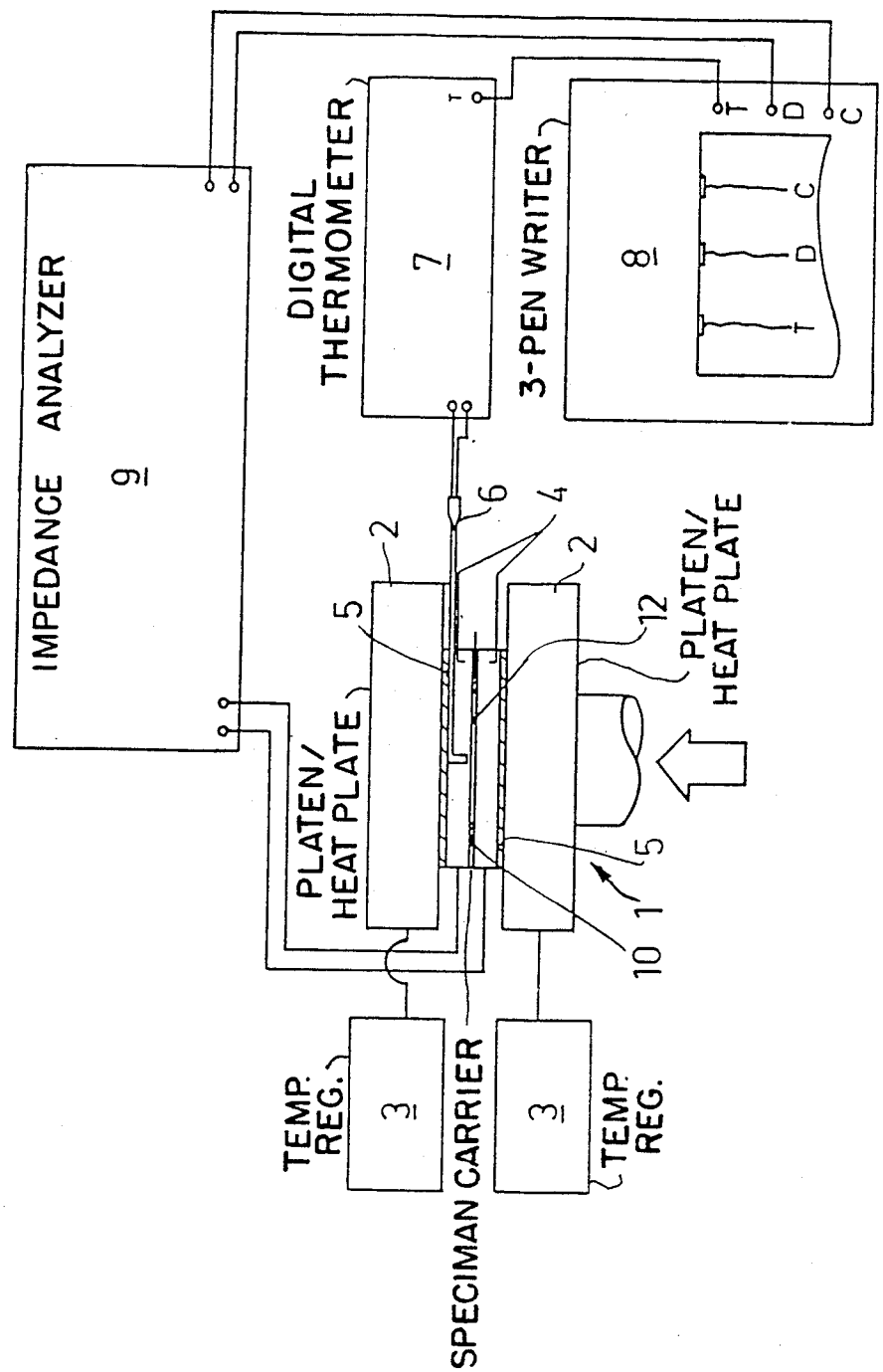

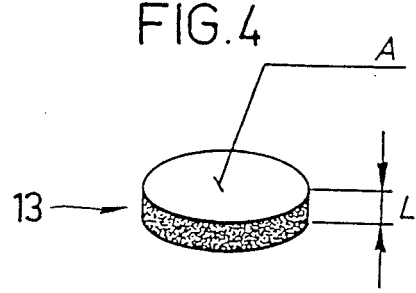
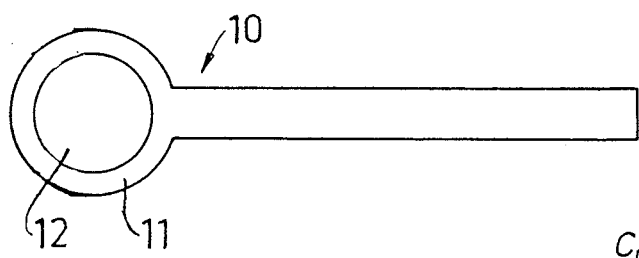
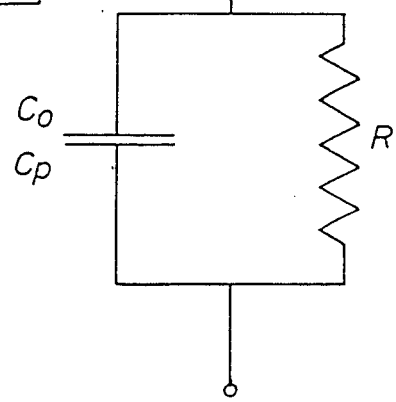
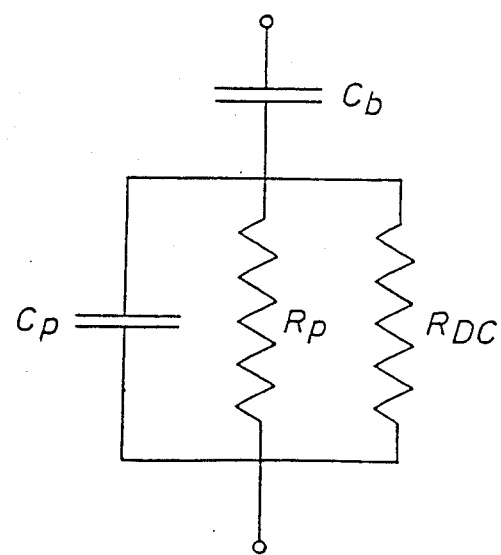

FIG.6
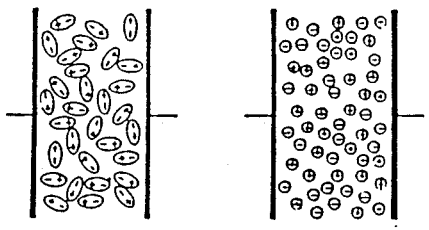
(a)
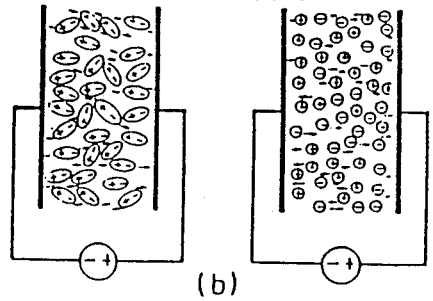
(b)
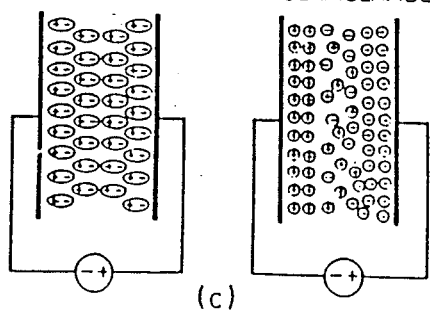
(c)

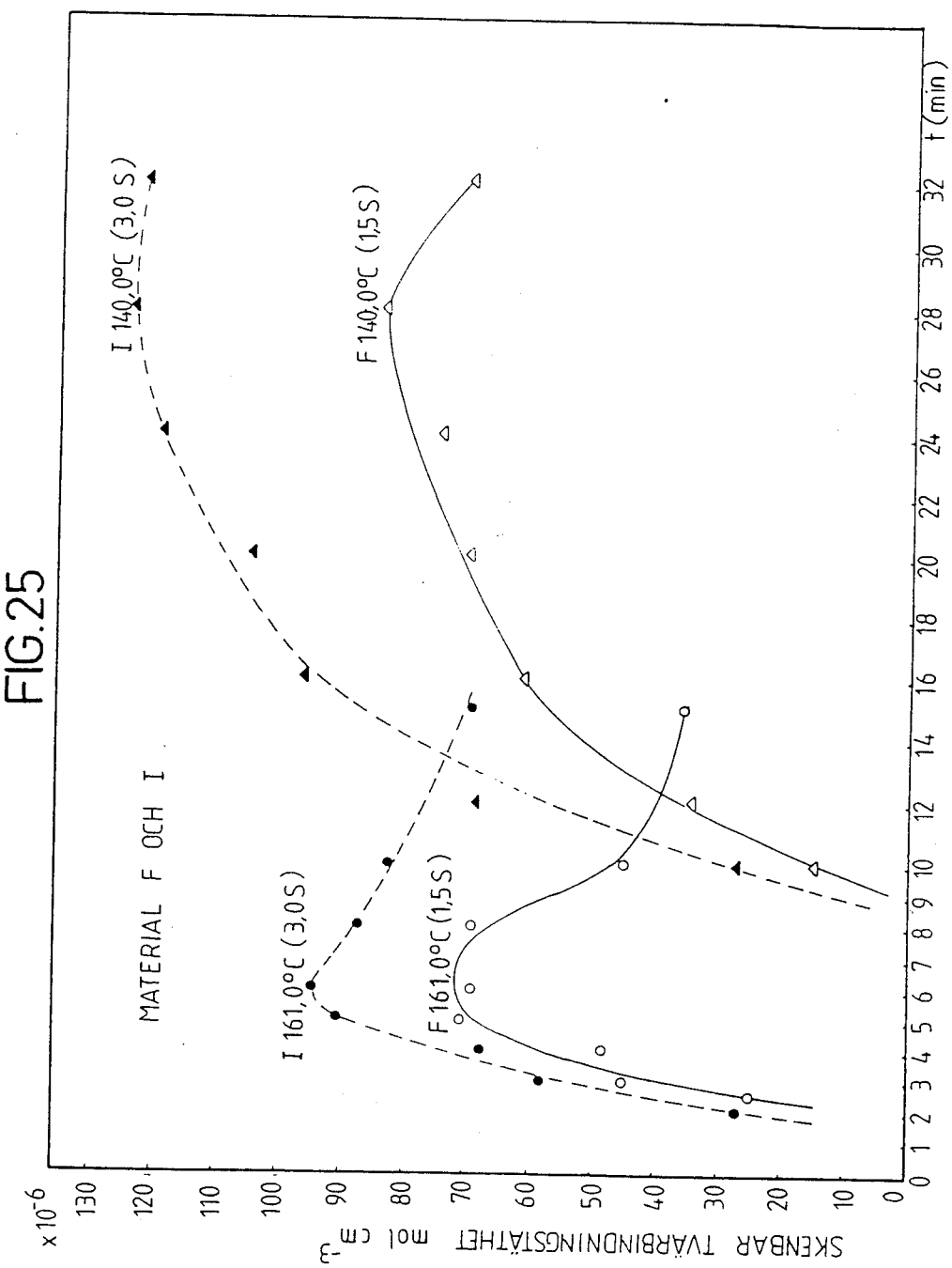

METHOD AND AN APPARATUS FOR DETERMINATION OF BASIC VALUES

BACKGROUND OF THE INVENTION

This invention relates to a method for determining basic values from a specimen of a dielectric material for analysis of its vulcanization characteristic and an apparatus for carrying out the method.

Polymers belong to the group of vulcanizable materials and the electric properties thereof have been the subject of relatively comprehensive studies and research for the major part of this century. These studies and research work have generated a great amount of knowledge about the interior structure of polymeric materials and how this is influenced by admixture of different additives such as plasticizers and organic or inorganic fillers. Dielectric measuring methods have also been used to a certain extent in studies of aging phenomena of polymeric materials. Controlling the vulcanizing or curing processes by means of the changes in the dielectric properties i.e. caused by crosslinking or curing reactions is not used much in practice and is nearly not used at all in rubber working technology.

At present the dielectric properties of different polymers are of interest in polymer working only because the dielectric losses can be utilized for generation of heat in connection with preheating or vulcanizing.

Despite the fact that the very earliest work in this special technique, below called vulcametry, was carried out as early as the end of the 1920's, the dielectric measuring methods have not yet had any real importance in vulcametry. This is partly because suitable measuring electrodes as well as directly recording measuring bridges have been lacking. However, the most obvious reason seems to be that the basic mechanisms about the influence of the crosslinking reactions on the dielectric relaxation phenomena are not yet known enough to be used in practical vulcametry.

As is well-known, a dielectric usually contains polarizable or polarized molecules or molecule groups having permanent or induced dipoles. In an electric field the dipoles are turned in the field direction and molecules containing permanent dipoles tend to orientate themselves in electric fields. How fast and to which extent this orientation takes place has to do with how the molecules interfere with each other. When a rubber material is vulcanized—crosslinked, a series of other side reactions except crosslinkages are formed in normal cases which are characteristic of each combination of rubber and vulcanizing agent. The formation and development of these reactions and reaction products can be followed by the aid of dielectric measuring methods. Thus, the dielectric vulcametry and consequently this invention are based on these changes in the polar properties of the vulcanized rubber.

A method developed about 1953 and described in U.S. Pat. No. 3,039,297 for continuous measurement of the crosslinking reaction in rubber mixtures is described in U.S. Pat. No. 3,039,297. This method can be said to be the start of modern vulcametry and is characterized in broad outline in that a continuous or periodic motion or force (tensile, compressive, shearing or torsional) is applied to a test specimen of unvulcanized rubber under simultaneous measurement of force and motion response, respectively. The force/movement is usually transferred to the test specimen by means of a rotor or a linearly movable paddle.

This method was accepted very rapidly and has become very popular which has generated a long series of different measuring apparatuses, which include "the Wallace-Shawbury Curometer", below called curometer, "the Cepar-Apparatus", "Viscurometer", "Vuremo", Zwick-Schwingelastometer" and that most known of all, viz. the so-called Monsanto-Rheometer, below called rheometer.

The original purpose of the technique here called vulcametry was quite simply to produce a functioning control method in the synthetical rubber industry rapidly growing in the post-war period. The vulcametry has thereafter also been found to be a very useful method for studying the reaction kinetics of the vulcanization process and has also been used for this purpose. However, in later years some criticism has been directed to this so-called traditional vulcametry which can be said to be mechanical. It has been shown that if the test specimen is heated relatively slowly and even after reaching temperature of equilibrium there are temperature gradients through the test specimen, that a non-desired sliding can arise between cavity and rotor and paddle, respectively, and that certain rubber materials have a tendency to become porous during the testing procedure.

Certain comparative studies with isothermal vulcanization which are considered to give acceptedly true values are described in Polymer Testing Vol. 1, No. 4, page 247, 1980 by R H Norman. It has also been shown that the rheometer gives a much longer vulcanization time than the curometer which, in turn, gives longer vulcanizatioin times than isothermal vulcanization. Examples of this are shown in the table below which indicates 90% of vulcanization time in seconds at different temperatures.

| Temperature °C. | Isothermal vulc. | Curometer | Rheometer |
| --- | --- | --- | --- |
| 120 | 3 120 | 4 800 | 7 800 |
| 140 | 870 | 1 100 | 1 800 |
| 160 | 280 | 320 | 460 |
| 180 | 72 | 105 | 195 |
| 200 | 17 | 47 | 97 |

The great differences at low temperatures apparent from the table are unexpected and are propably due to the fact that there is a considerable difference between the true average temperature of the test specimen and the measured temperature even after a very long period of time. On the other hand, the great difference at high temperatures is not directly unexpected. It has been shown that the rheometer in comparison with guaranteed isothermal conditions gives vulcanizing times that are about twice as long at most temperatures. There are two probable explanations of these substantial deviations. Firstly, heat is continuously lost as heat is diverted from the rotor via the rotor shaft to the drive unit of the rheometer, with the result that the rotor becomes colder than the rotor cavity. Due to this the average temperature of the rubber specimen will be considerably longer than the adjusted temperature and therefore the vulcanization process will proceed more slowly. Secondly, it will take a longer time to heat the specimen in a rheometer in comparison with the conditions prevailing when producing the isothermal results shown in the above table due to the fact that the test specimen in the rheometer is much thicker than 0.5 mm which is the thickness of the specimen used in the isothermal tests.

Another disadvantage of conventional vulcametry is the interpretation problems arising when data produced by the rheometer are to be used to determine vulcanization times of voluminous rubber products such as big rubber dampers, contract tires, mill linings etc. Therefore there is a great demand for a method or process enabling measurement of the vulcanization course directly during the vulcanization of the current products.

SUMMARY OF THE INVENTION

It is therefore the object of the invention to provide a method and an apparatus for carrying out the method enabling measurement of vulcanization course directly during the vulcanization in a quick and safe manner and giving true measured values as a result.

This object is achieved by the method and the apparatus of the present invention which measures the relative permittivity $\epsilon'_r$ and dielectric loss factor $\epsilon''$ of the rubber as a function of the time at a frequency of at least 10 kHz and preferably at a higher frequency. For instance between 200 and 300 kHz, while rubber is vulcanized at an elevated temperature, for instance between 120° and 190° C.

BRIEF DESCRIPTION OF THE DRAWINGS

FIG. 1 shows schematically and in the form of blocks an apparatus of the invention for carrying out the method, FIG. 2 is a plane view of a specimen carrier according to the invention, FIG. 4 shows a circular, plane-parallel capacitor of the type obtained in a process of the invention, FIG. 5 shows an equivalent diagram or circuit of said capacitor, FIGS. 6a, 6b and 6c show how dipoles and ions orientate themselves in a material to which an electric voltage has been applied, FIG. 7 shows an equivalent diagram of a capacitor containing a dielectric having a high leakage and a tendency to form blocking layers, FIGS. 14–25 show additional curves for illustrating the invention, these curves being defined more in detail in the specification.

DETAILED DESCRIPTION OF THE PREFERRED EMBODIMENT

Vulcanization does not proceed in general as a simple chemical reaction but consists of a series of complex reactions that in certain connections may require hours to complete.

Sulphur and substances giving off sulphur are not the only chemical substances participating in these reactions but other substances such as metal oxides, fatty acids and organic accelerators also take part actively in the crosslinking reaction. The organic accelerators do not operate as usual catalysts that do not participate actively in the vulcanizing reaction. The main task of the accelerators is to activate the sulphur and as distinguished from usual catalysts the accelerators undergo chemical changes.

Accelerated sulphur vulcanization is generally considered to proceed according to the following steps described:

(a) The accelerators react with sulphur forming monomeric polysulfides Ac—$S_x$—Ac where Ac is an organic radical formed from the accelerator.

(b) The polysulphides can react with rubber forming polymeric polysulphides of the following structure: rubber—$S_x$—Ac.

(c) The polymeric polysulphides either react directly or via intermedia forming polysulphidic crosslinkages between the rubber molecules according to: rubber—$S_x$—rubber.

Figure 3:
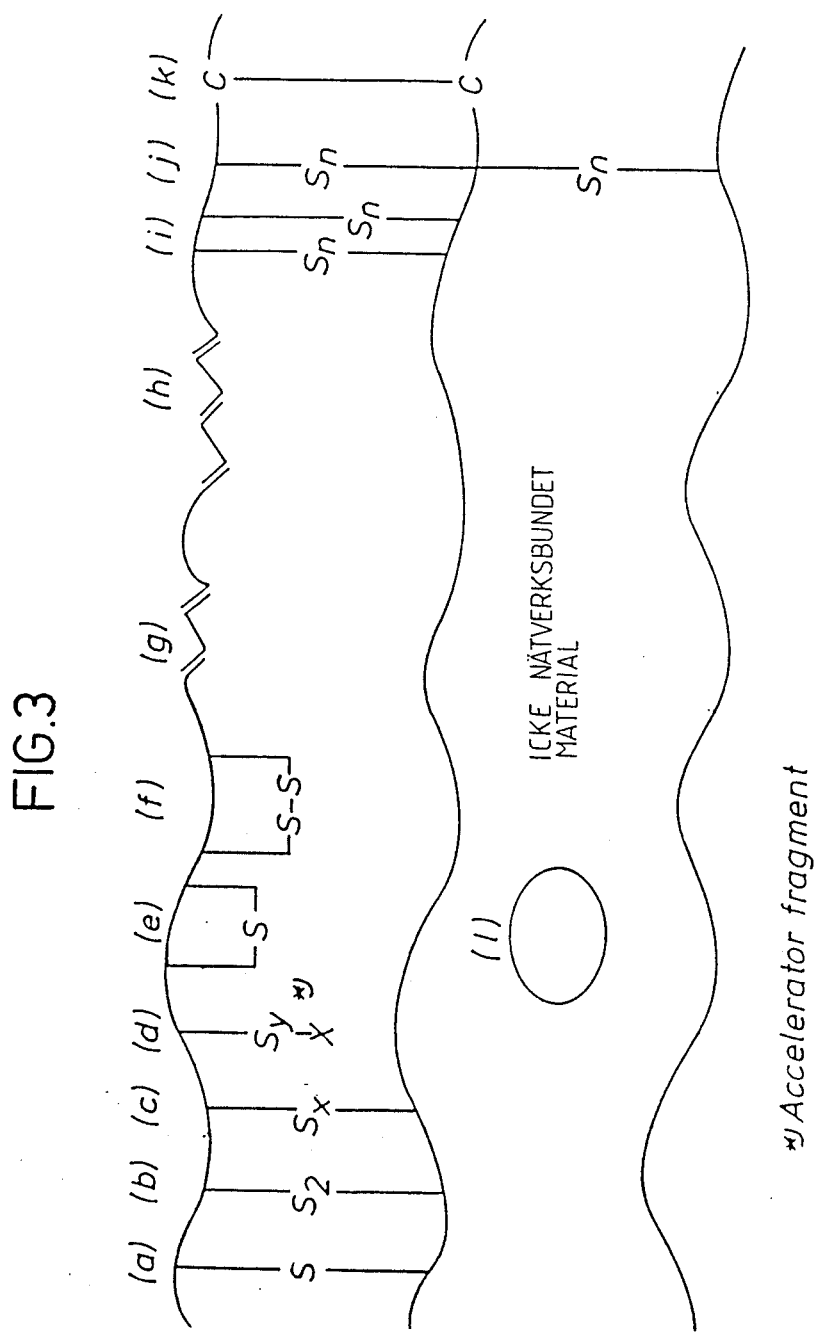
FIG. 3 shows examples of structures formed between molecule chains and on these in vulcanization.

Examples of the multiplicity of structures formed between the molecule chains (intermolecularly) and on the molecule chains (intramolecularly) appear from FIG. 3.

In the general case shown in FIG. 7 not only (a) mono-, (b) di-, and (c) polysulphidic crosslinkages are formed in diene rubbers (i.e. rubbers containing conjugated double bonds) but also (d) sulphidic groups with accelerator fragments in side position, (e) intraemolecular cyclic mono- and (d) disulphides, (g) conjugated dienes and (h) trienes, (i) parallel adjacent crosslinkages, (j) crosslinkages bonded to the same or adjacent carbon atoms, (k) c—c bonds (probably do not exist) and (l) not crosslinked material.

In vulcanization the poly- and disulphidic crosslinkages formed initially undergo a series of maturity reactions.

The polysulphidic crosslinkages and the laterally positioned polysulphidic groups undergo desulphurizing reactions to be reformed to di- and gradually monosulphidic crosslinkages and groups.

Before the final formation of the thermally stable monosulphidic crosslinkages and groups takes place the di- and polysulphidic crosslinkages can undergo thermal reactions, sulphurous products such as cyclic sulphides for instance being formed.

Several of the reactions between sulphur and substances giving off sulphur described above increase the polarity of the network formed. The formation and changes of these polar groups during vulcanization reactions are utilized in accordance with the principles on which the invention is based to follow the vulcanization.

According to the invention the apparatus for these measurements and consequently for determining the required basic values from a specimen of a vulcanizing material to be analyzed comprises a press 1 having a press minimum pressure of 200 kPa and two platens 2 which can be heated and the temperature of which is adjusted by means of a temperature regulator 3 for each thereof. Each platen or heat plate 2 is provided with an electrode plate 4 of aluminum galvanically separated from the associated heat plate 2 by means of a layer 5 of teflon foils. This layer 5 need not be thicker than 1 mm. To the upper electrode plate 4 a thermoelement 6 is connected by means of which the temperature of said electrode plate 4 is measured and the tip of which is placed at a small distance, for instance 0.3 mm, inside the surface of the electrode plate 4. The thermoelement 6 is galvanically separated from the electrode plate 4 by means of a very thin coating of silicone rubber and is connected to a digital thermometer 7 with analog output which, in turn, is connected to the temperature input T of a 3-pen writer 8.

Moreover, each of the electrodes plates 4 is connected to an impedance analyzer 9 by means of which capacity C and dielectric loss coefficient D (tan δ) are determined and which can have a frequency range between 5 Hz and 13 MHz. The impedance analyzer 9 is connected with its outputs to the capacity input C and dielectric loss coefficient input D of the 3-pen writer.

The apparatus also includes a specimen carrier 10 consisting of a ring 11 provided with a handle made of an electrically non-conductive material such as teflon with an opening or measuring cavity 12 therein. The volume of the carrier 10 in which the material specimen is placed is defined after introducing the specimen carrier 10 between the electrode plates 4 of the press 1.

In order to achieve the best possible measuring result in the shortest possible time the material specimen should have the smallest possible volume and thickness and this is obtained in accordance with the invention thanks to the fact that the specimen carrier can be made very thin and even thinner than 0.25 mm. The measuring cavity 12 of the specimen carrier 10 shown in FIG. 2 has for instance a volume only amounting to 0.28 cm$^3$. The predetermined volume of the measuring cavity 12 is relatively simple to determine, for instance by weighing the size of the material specimen that it will fill up the measuring cavity 12 exactly in pressing.

In accordance with the invention the empty specimen carrier 10 is placed between the heated electrode plates 4 of the open press 1 after which the press 1 is closed and kept closed until the test specimen 10 has been heated to the current testing temperature. After only a few seconds the specimen carrier 10 will take the temperature of the electrode plates 4, and thereafter the press 1 is opened and a material speciment prepared in advance is placed as fast as possible on the lower electrode plate 4 and as centrally as possible within the measuring cavity 12 of the specimen carrier. The press 1 is thereafter closed again and the air pressure is rapidly increased to the intended value, for instance 200 kPa. This value for the pressure has been found to be sufficient to press out the specimen consisting of unvulcanized rubber so that the specimen will fill up the measuring cavity 12 of the specimen carrier enclosed by the electrode plates 4 completely at the same time as it prevents porosity from arising in the specimen. Thanks to the fact that the pressed-out specimen becomes very thin, for instance 0.25 mm, it is heated very rapidly, i.e. within less than half a second, a time that is so short that it can be completely neglected in comparison with the normally current vulcanization times. As soon as the press has closed the capacity values C, tangent δ-values of dielectric loss coefficient D and temperature values T start to be automatically recorded by the 3-pen writer 8.

Thus, these values derive from the body of vulcanized rubber located within the specimen carrier 10 which body forms together with the two electrode plates 4 a circular, plane-parallel capacitor 13 (FIG. 4). The relative permittivity $\epsilon'_r$ and dielectric loss factor $\epsilon''$ of which can be easily calculated by means of the resulting values of capacity and loss angle. It should be noted that no separation films have been used between the electrode plates 4 and the dielectric (the vulcanized rubber) and this is an advantage as such films have been found to give measuring results that are strongly influenced whether the film is charged or discharged through the bulk resistance of the dielectric.

As is well-known, the capacity of a plane-parallel capacitor of the type for instance shown in FIG. 4 is determined by the surface A of the electrode plates and their mutual distance L. A capacitor thus consisting of two electrode plates with the surfaces A having a mutual distance L and containing a homogeneous dielectric, the vulcanized rubber in this case, with the relative permittivity $\epsilon'_r$ and loss factor $\epsilon''$ can be described by means of an equivalent diagram or circuit 14 of the type shown in FIG. 5. This circuit is built of the capacitor $C_p$ which is connected in parallel with the resistance R. The capacity of $C_p$ and the resistance R can be written $$C_p = \epsilon_0 \epsilon'_r A/L; \quad \epsilon'_r = C_p/C_o \qquad \text{Equ. (1)}$$

$$R = L/w \times A \times \epsilon'' \times \epsilon_0 \qquad \text{Equ. (2)}$$

where
$\epsilon_o$ = the vacuum permittivity
$\omega$ = the angular frequency
$C_o$ = the capacity of an empty capacitor
$C_p$ = the capacity of a capacitor containing a dielectric.

By reforming the equations (1) and (2) explicit expressions of $\epsilon'_r$ and $\epsilon''$ are obtained.

$$\epsilon'_r = \frac{C_p \times L}{A \times \epsilon_o} \qquad \text{Equ. (3)}$$

$$\epsilon'' = L/ARw\epsilon_o \qquad \text{Equ. (4)}$$

It is apparent from the equations (3) and (4) that the relative permittivity $\epsilon'_r$ is not actuated by the resistive component R while $\epsilon''$ is influenced.

Polymers in general and polymers containing electrically conductive substances such as carbon black in particular can transport charges if an electric voltage is applied across the material (the dielectric), see FIG. 6.

The resistivity of a dielectric and its tendency to form blocking layers at the surfaces of the electrode plates influence the dielectric properties of the material. Dielectrics having a low resistivity are said to have a high leakage.

The equivalent diagram of a capacitor containing a dielectric with a high leakage and having tendencies to form blocking layers is apparent from FIG. 7.

The part of the resistance ($R_{DC}$) caused by charge transport is independent of the frequency of the electric field applied across the capacitor as distinguished from the part of the resistance ($R_p(W)$) caused by the dipolar relaxation. If the current through a dielectric is caused by charge migration the resistance of the dielectric can be characterized by its bulk resistivity. The two charged layers formed at the surfaces of the electrode plates have in FIG. 4 been combined to a blocking capacitor $C_b$ which is connected in series with the circuit conneted in parallel formed by $C_p$, $R_p(w)$ and $R_{DC}$.

The loss factor $\epsilon''$ can then be written $$\epsilon'' = \frac{1}{wC}\left(\frac{1}{R_{p(w)}} + \frac{1}{R_{DC}}\right) = \frac{1}{Aw}\left(\frac{1}{R_{p(w)}} + \frac{1}{R_{DC}}\right) \qquad \text{Equ. (5)}$$

$R_{DC}$ being the resistance caused by charge transport and $R_{p(w)}$ being the resistance caused by the dipolar relaxation.

The dipolar parallel resistance $R_{p(w)}$ goes towards infinity when the frequence goes towards zero while $\epsilon''$ will increase due to the D.C. conduction when the frequency decreases.

If the conductivity of the dielectric is so high that the impedance of R is less than the impedance $R_c$ of C $$R_c = L/wA\epsilon'_r\epsilon_o \qquad \text{Eqv. (6)}$$

$\epsilon''/\epsilon'$ will be tan $\delta > 1$ with the result that the charge of $C_b$ through R will dominate the electric behaviour of the circuit.

The electrode polarization, i.e. the charge of $C_b$, will not influence the characteristic of the electric circuit as long as R is greater than $R_c$. It can be concluded from this that electrically isolating separation films between the dielectric and the electrode plates, which sometimes have been used in similar connections, should not be used so that these films disturb or usually make correct measurements completely impossible.

The function of the present method and how the measurement results obtained correlate with the corresponding ones from other known and established measuring methods is described more in detail in the following by the aid of some examples.

Example 1 concerning natural rubber mixtures A, B and C with conventional sulphur/accelerator systems and retardants (Santogard PVI-50) and having a composition according to the following table 1:

|  | A | B | C | D |
|---|---|---|---|---|
| NR SMR CV 60 | 100 | = | = | = |
| Carbon black N220 | 45 | = | = | = |
| Dutrex 729 HP[1] | 8 | = | = | = |
| ZnO | 4 | = | = | = |
| Stearic acid | 1 | = | = | = |
| TMQ[2] | 1.5 | = | = | = |
| 6 PPD[3] | 1.5 | = | = | = |
| Microcrystalline wax | 2 | = | = | = |
| CBS[4] | 0.8 | = | = |  |
| Sulphur | 2 | = | = |  |
| PVI-50[5] | — | 0.5 | 0.8 |  |
| TMTD[6] |  |  |  | 1 |
| DTDM[7] |  |  |  | 1 |

[1]Aromatic oil
[2]Polytrimethyl-dihydrochinoline
[3]Dimethylbutyl-phenyl-p-phenylene diamine
[4]N—cyclohexyl-2-benzothiazyl-sulfenamide
[5]Cyclohexylthiophthalimide CTP
[6]Tetramethylthiuram disulfide
[7]4,4'-dithiomorpholine The mixtures shown in the table are typical of such mixtures of natural rubber used in industry for the manufacture of for instance automobile tires. The mixtures A, B and C are identical except for the fact that the mixtures B and C contain small amounts—0.5 phr and 0.8 phr, respectively—of a retardant (Santogard TM PVI-50) moving the vulcanization start towards lower times. The mixture D is also identical to the mixture A except for the fact that the coventional sulphur/accelerator vulcanization system in mixture A has been exchanged for an accelerator/sulphur donor vulcanization system. Such systems are generally designated EV-(Efficient vulcanization) systems.

Figure 8:
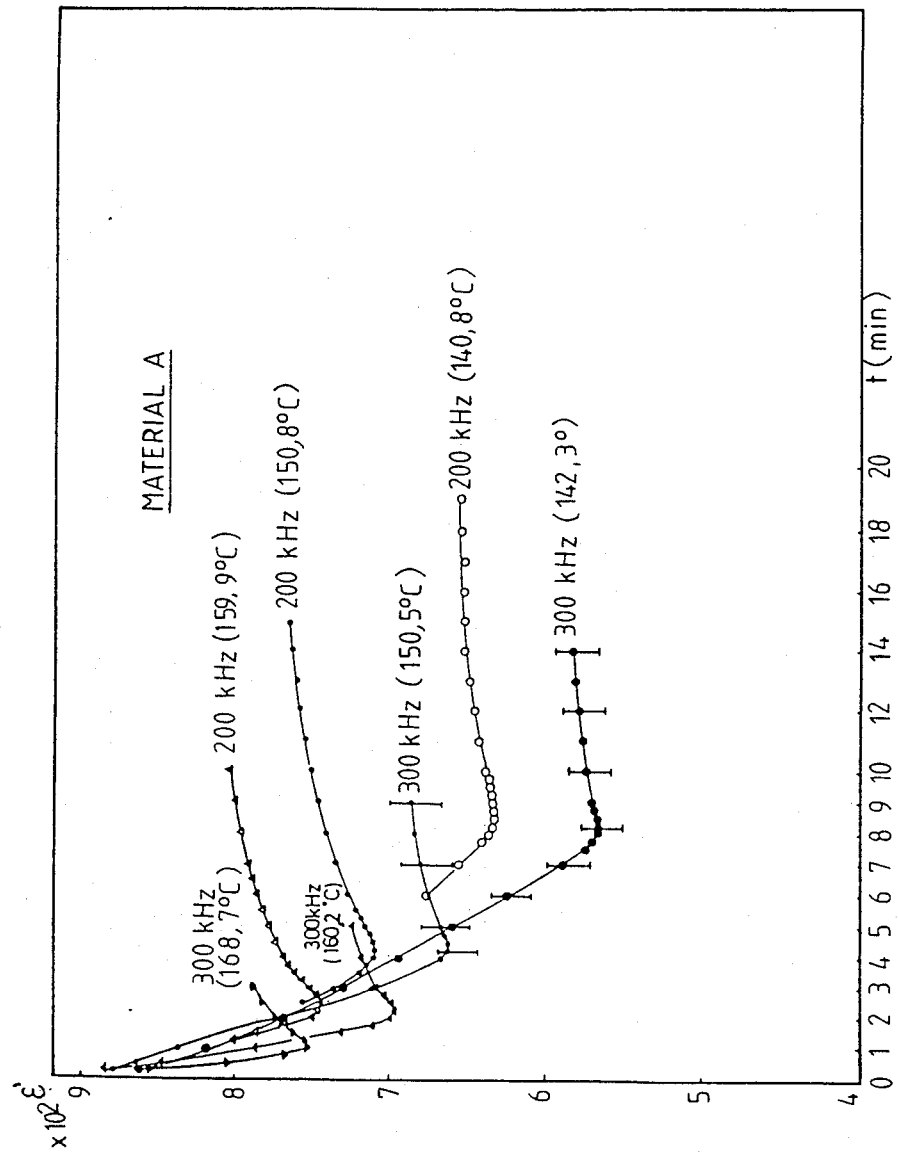
FIGS. 8–14 show different curves, that is to say so-called dielectric curo- or vulcograms, of $\epsilon'$ or $\Delta\epsilon'$ as a function of the time at different temperatures and frequencies of different rubber mixtures
Figure 9:
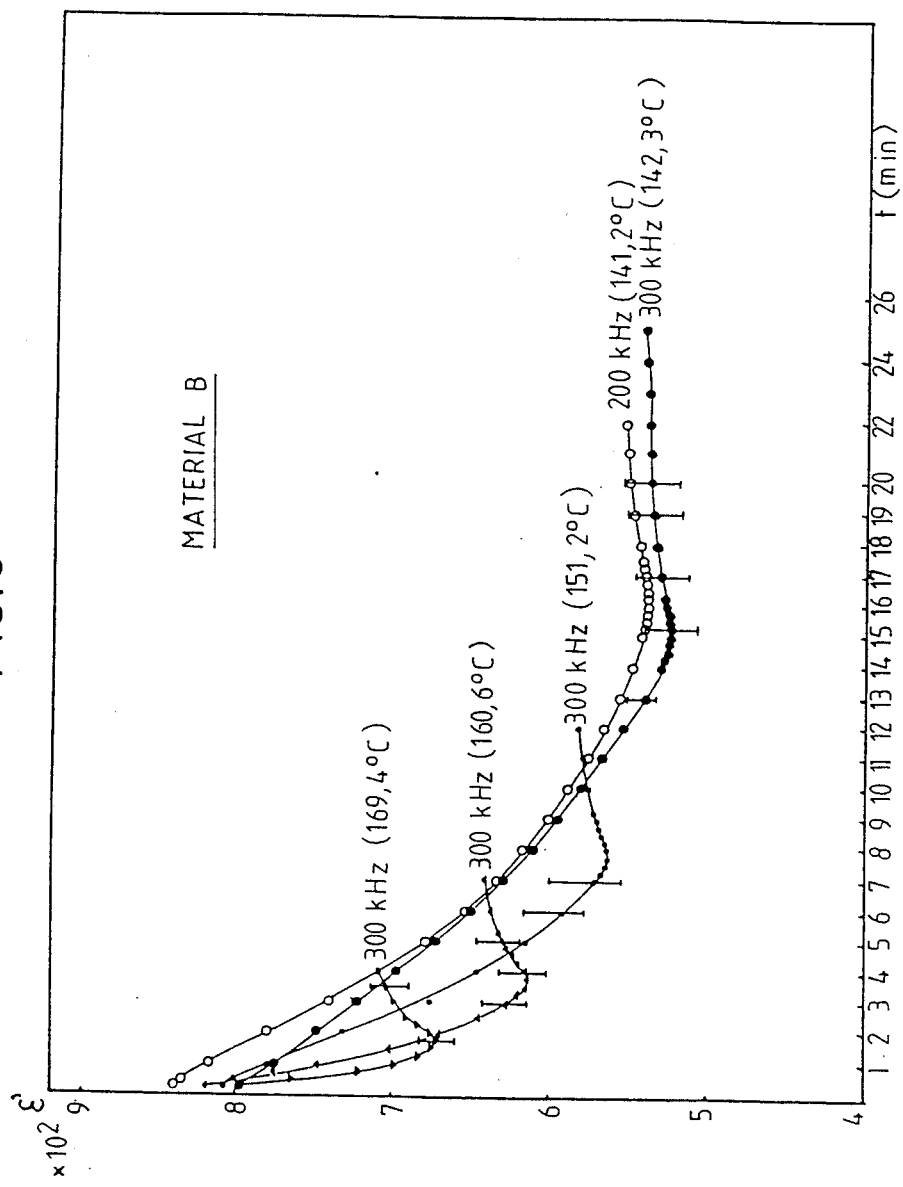
Figure 10:
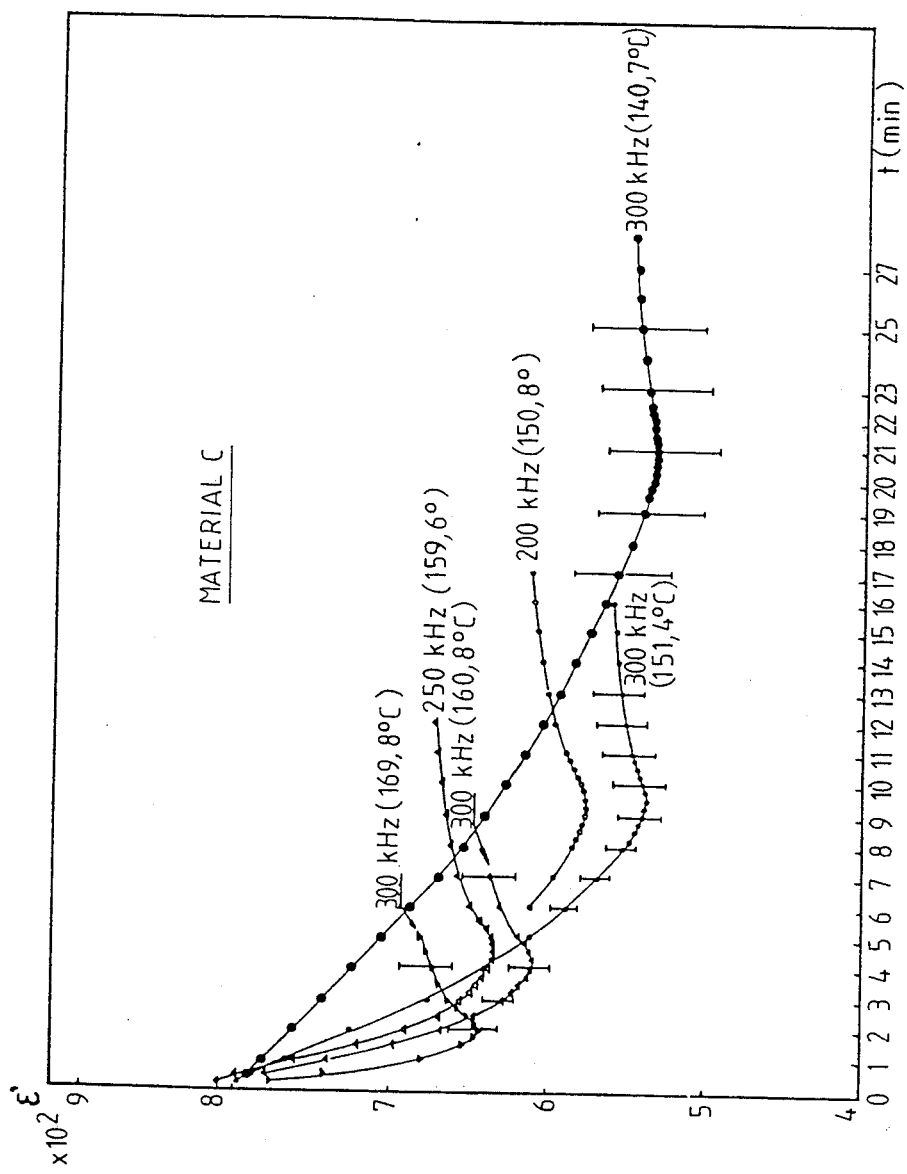

On the basis of the basic values obtained by means of the method and apparatus of the invention different curves can be obtained and a nunber of such curves is shown in FIGS. 8-24. In the following some of these curves are called dielectric curo- or vulcograms showing $\epsilon'_r$ as a function of the time at different temperatures and frequencies and for the mixtures A, B and C such curograms are shown in FIGS. 8, 9 and 10.

The dielectric curograms of the mixtures A, B and C have all the same form as in the sense that $\epsilon'_r$ decreases initially to start to increase again via a minimum point ($\epsilon'_{r\,min}$). The time up to $\epsilon'_{r\,min}$ is also dependent on the composition of the mixture and temperature in such a way that a higher temperature gives shorter times to $\epsilon'_{r\,min}$ and that the retarded mixtures (B and C) give longer times to $\epsilon'_{r\,min}$ than the non-retarded mixture A.

To find inflection points dependent on temperatures, frequency and retardance in the dielectric curograms was unexpected considering the fact that the measuring cavity 12 is filled with a material—a dielectric—having a relative permittivity $\epsilon'_r$ being in the range 500–1900 depending on temperature and frequency.

As the capacitance of a plane-parallel capacitor, as previously mentioned, is proportional to the surface of the dielectric and inversely proportional to its thickness it is very important that the geometric form of the dielectric is kept at a constant. Sometimes this has been relatively difficult to accomplish because a small displacement of the position of the rubber specimen in the specimen carrier 10 and small variations of the weight of the specimen may cause the rubber to flow asymetrically in the specimen carrier 10 with the result that part of the rubber will flow out of the specimen carrier on one side at the same time as a waste is formed on the other side or that the specimen carrier is filled either too much or too little. The effect of this is that both the surface and the tnickness of the dielectric can vary a little if a great deal of care is not taken on preparation and placement of the specimen in the specimen carrier 10.

If an analysis method, especially one that is intended for routine analyss, might be accepted it is required that the preparation of the specimen should be simple. To avoid the problem with the $\epsilon'_r$-values being displaced due to the fact that the size and thickness of the dielectric vary a little the measured values can be normalized in the following way. Instead of using absolute values of $\epsilon'_r, \Delta\epsilon'_r$-values can be calculated by subtracting the lowermost $\epsilon'_r$-value, i.e. the $\epsilon'_r$-value at the inflexion point, from all following $\epsilon'_r$-values.

$$\Delta\epsilon'_r = \epsilon'_r\,t \geq \text{inflex.} - \epsilon'_r\,\text{inflex.} \qquad \text{Equ. (7)}$$

$\Delta\epsilon'_r$ is then plotted as a function of the time.

Figure 11:
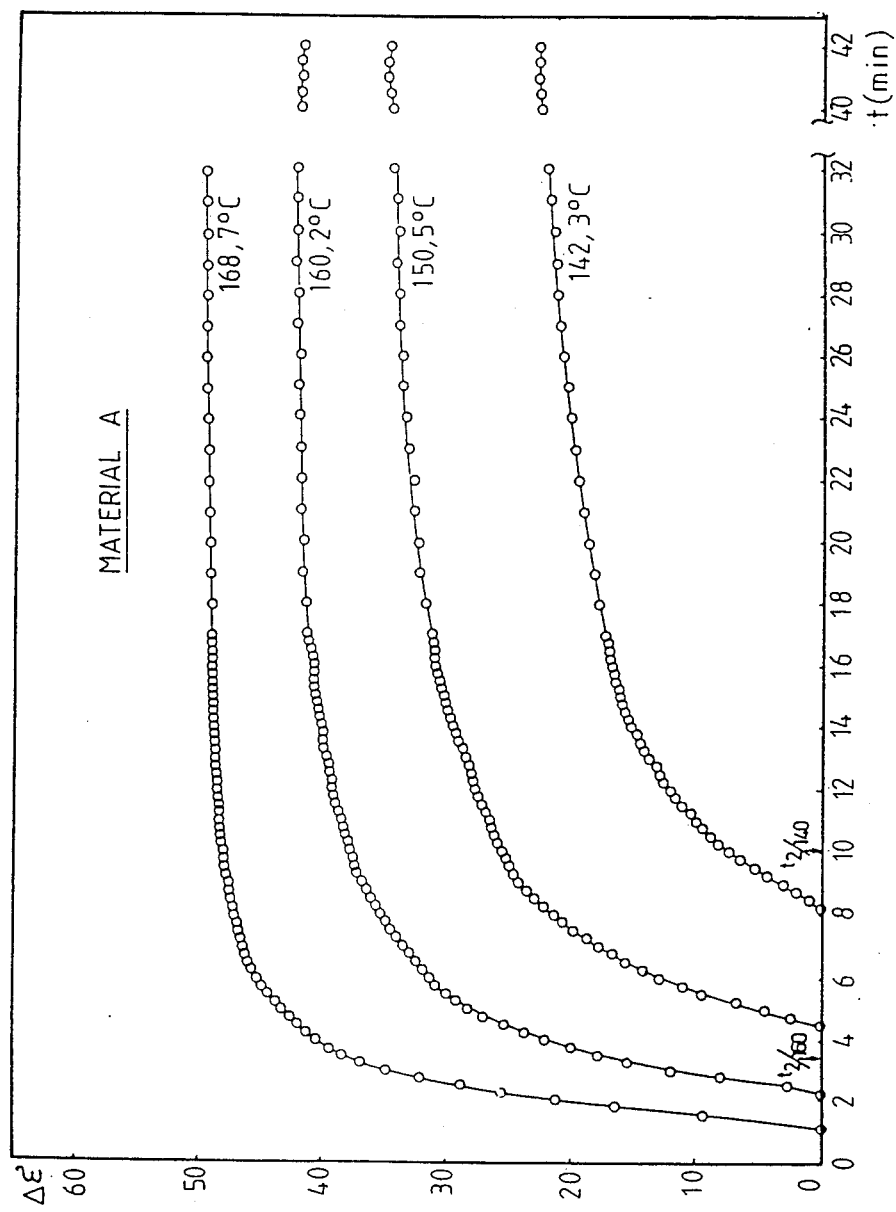
Figure 12:
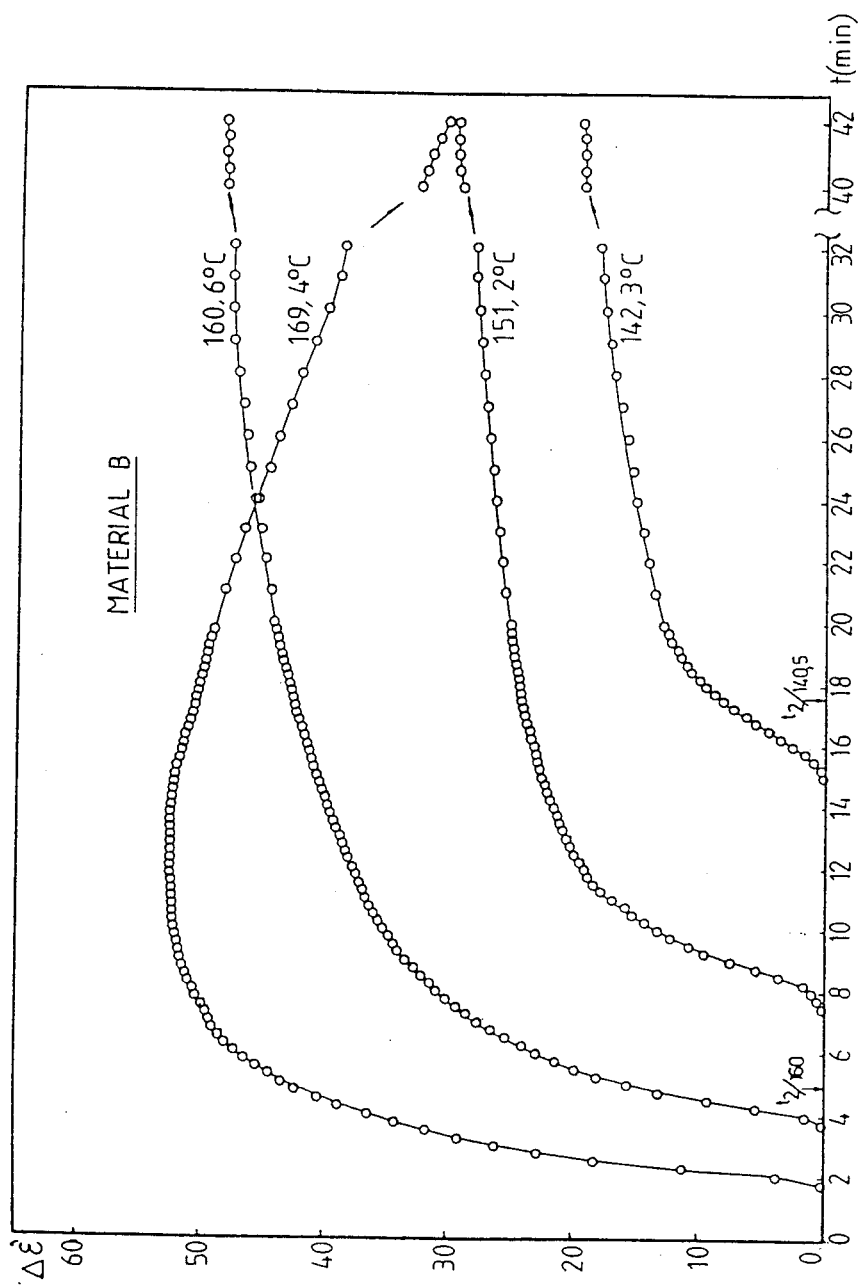
Figure 13:
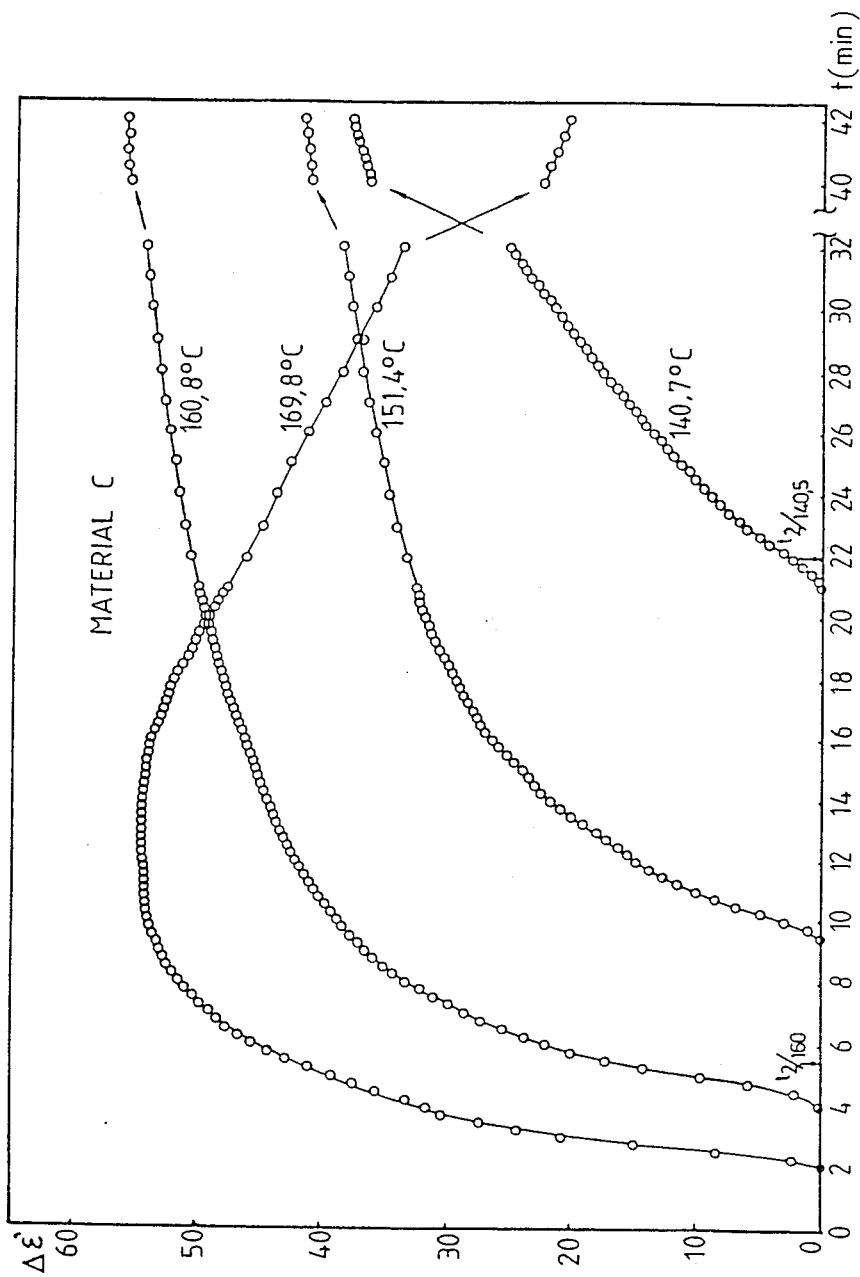

In FIGS. 11, 12 and 13 $\Delta\epsilon'_r$-values calculated according to equ. (7) for the mixtures A, B and C from data recorded at 300 kHz have been plotted as a function of the time at four different vulcanization temperatures.

For the mixtures A, B and C vulcanized at about 140°, 150° and 160° C. the $\Delta\epsilon'_r$-values increase monotonously, especially at the lower vulcanization temperatures. Higher vulcanization temperatures always give a higher initial inclination of the $\Delta\epsilon'_r$-curves than lower temperatures which shows that the inter- and intramolecularly bonded sulphur gives a chemical structure of the network that becomes more polar with higher vulcanization temperature.

At about 170° C. $\Delta\epsilon'_r$ increases for the mixtures B and C initially to decrease again via a maximum. At present it is not known why mixture A does not show the same behaviour as B and C at about 170° C. The reason may possibly be that the retardant Santogard PVI-50 included in the mixtures B and C influences the chemical structure of the network.

In order to investigate what the correspondence of the inflection points in the curograms in FIGS. 8, 9 and 10 or the zero-values ($\Delta\epsilon'_2=0$) in FIGS. 11, 12 and 13 in the vulcanization of the test specimens, a great number of specimens are vulcanized at the temperatures used at recording of the dielectric curograms. Part of the specimens was vulcanized for a somewhat shorter time or the same time to which the time corresponds necessary to reach the $\epsilon'_r$-minimum or the time to reach $\Delta\epsilon'_r=0$. A larger number of test specimens was vulcanized for longer times than the time necessary to reach the $\epsilon'_r$-minimum. The crosslinkage density of the specimens was determined by swelling the specimens in dichloromethane for 6 days at room temperature, after which the cosslinkage density was calculated by means of Flory-Rehner's equation. The influence of the carbon black on the crosslinkage density has been compensated by means of the correction factors indicated by Kraus (12).

Figure 14:
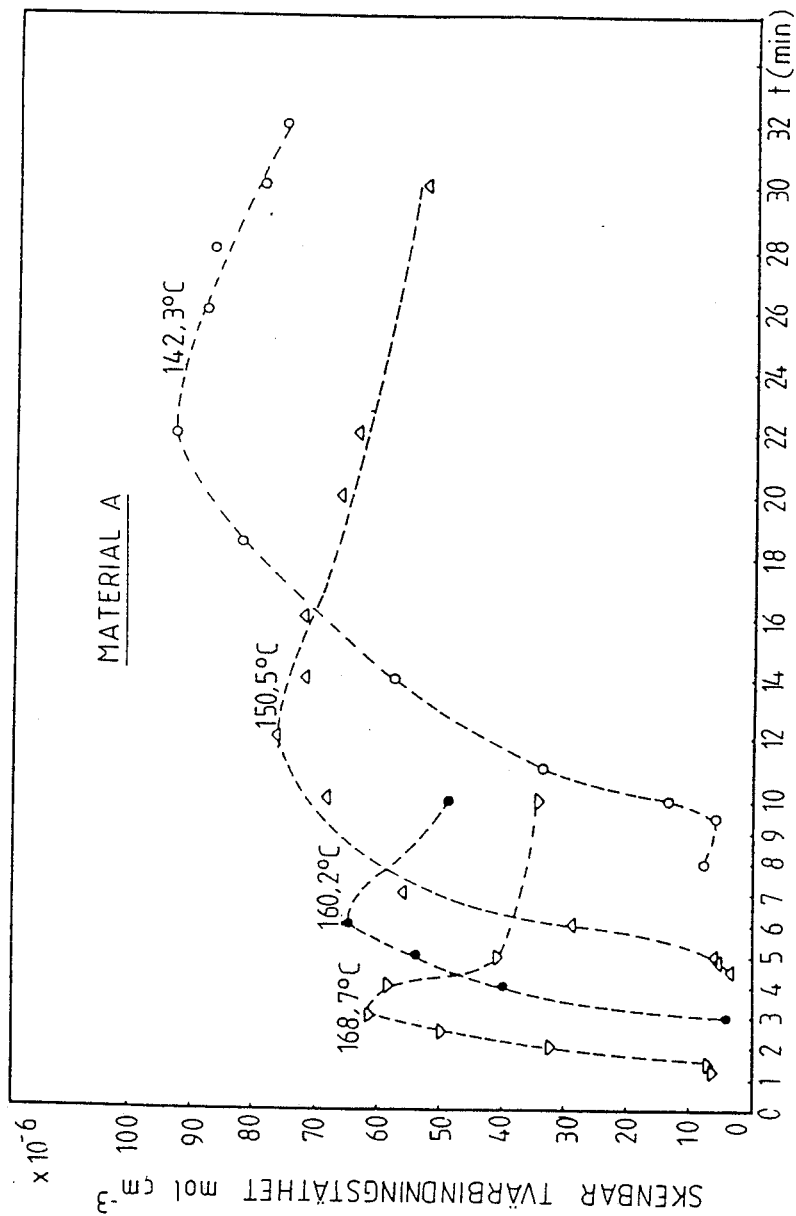
Figure 15:
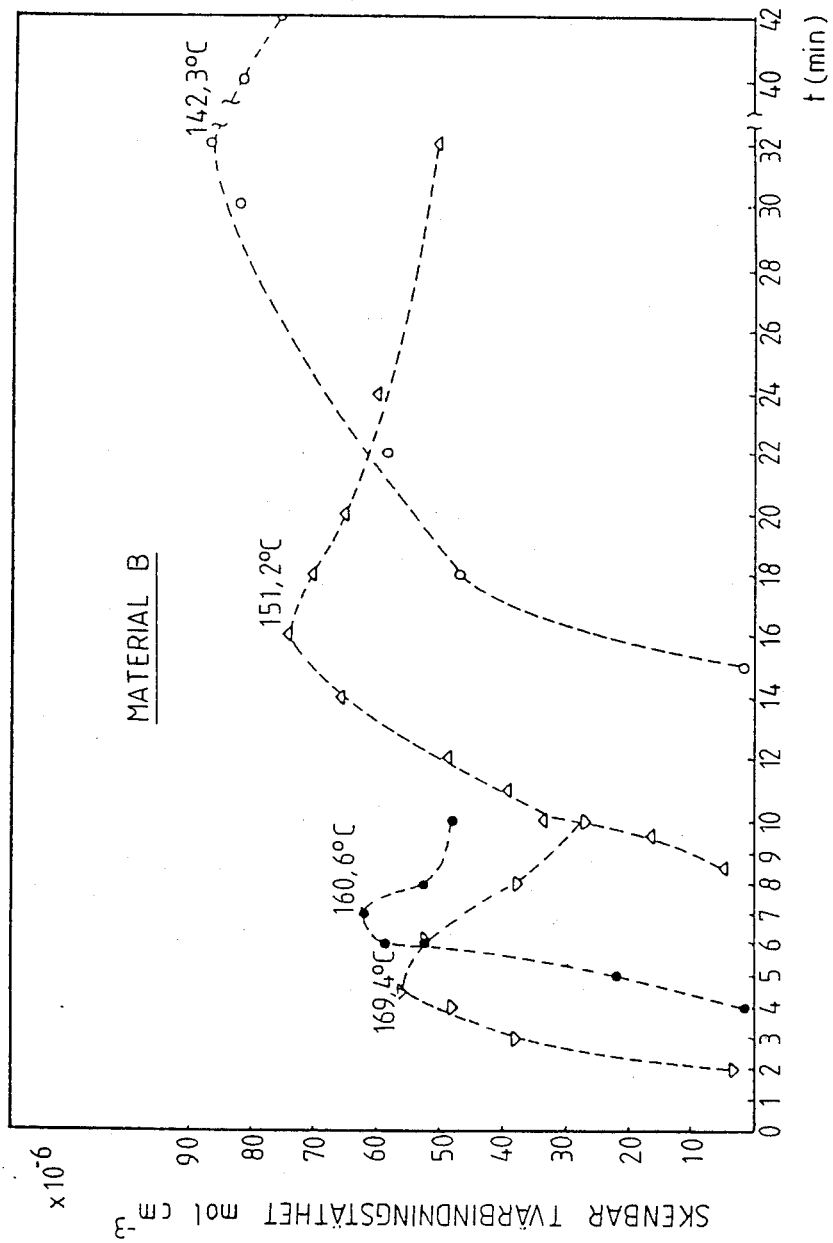
Figure 16:
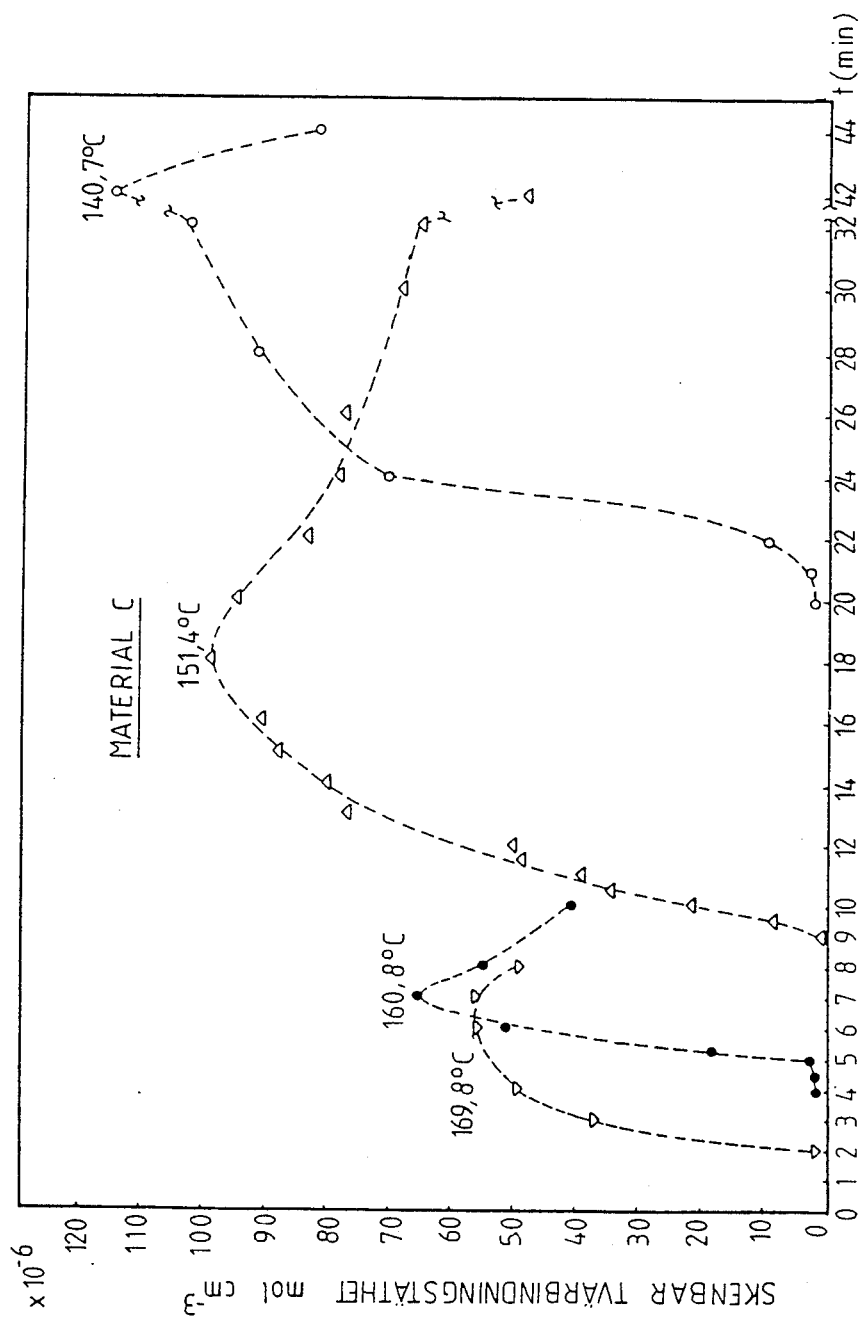

The change of the crosslinkage density as a function of the vulcanization temperature and the time is shown in FIGS. 14, 15, 16 for the mixtures A, B and C.

Figure 17:
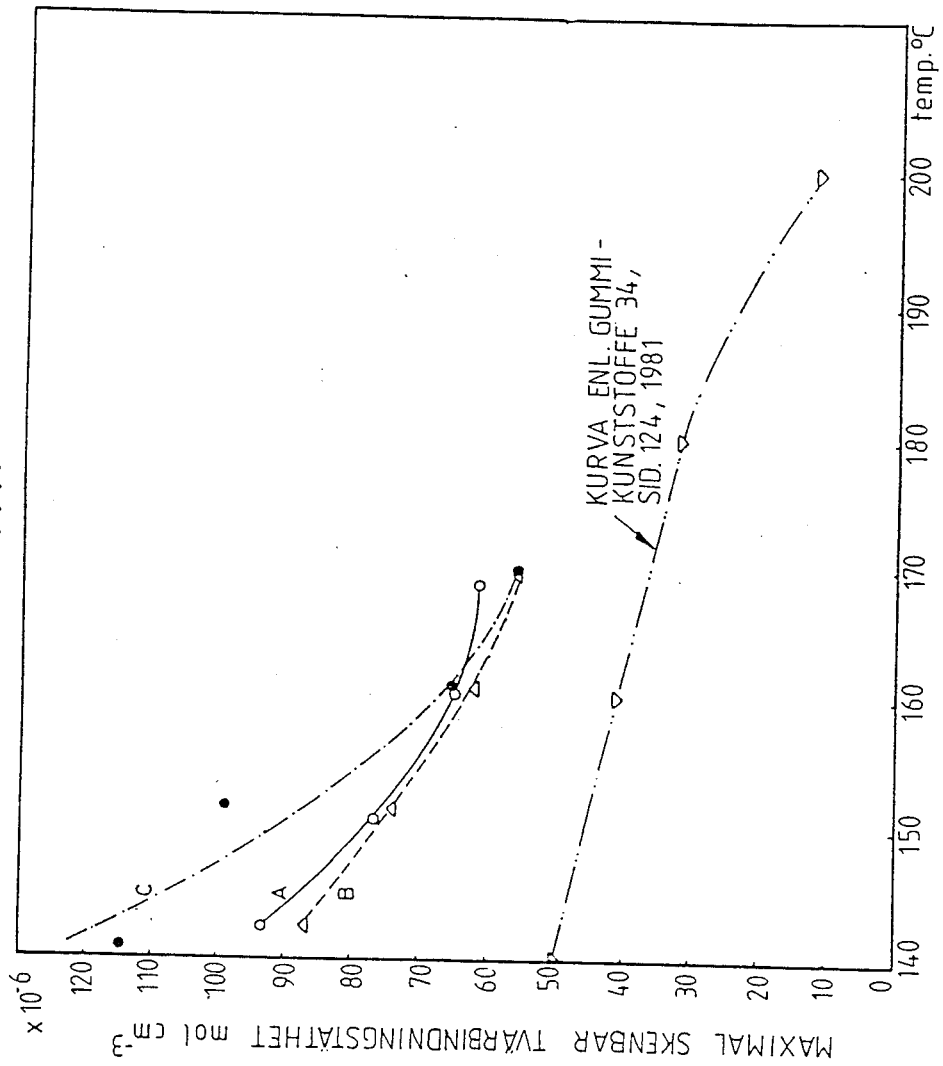

The results obtained are typical of natural rubber that has been vulcanized by means of conventional sulphur vulcanization systems in the sense that the maximum crosslinkage density will decrease when the vulcanization temperature increases, as is apparent from FIG. 17.

The rate at which the number of effective crosslinkages decreases as a function of the vulcanization temperature over a large temperature range (140° C.-200° C.) of a typical sulphur-vulcanized natural rubber mixture is also shown in FIG. 17. Data for this later curve has been taken from Gummi Asbest Kunststoffe 34, page 124, 1981, E. R. Rodger.

As is apparent from the figures the agreement between the times up to the start of the vulcanization which has been determined chemically (FIGS. 14, 15 and 16) and the times up to the $\epsilon'_r$-minimum values determined dielectrically (FIGS. 8, 9, 10 and 11, 12, 13) is very good.

Figure 18:
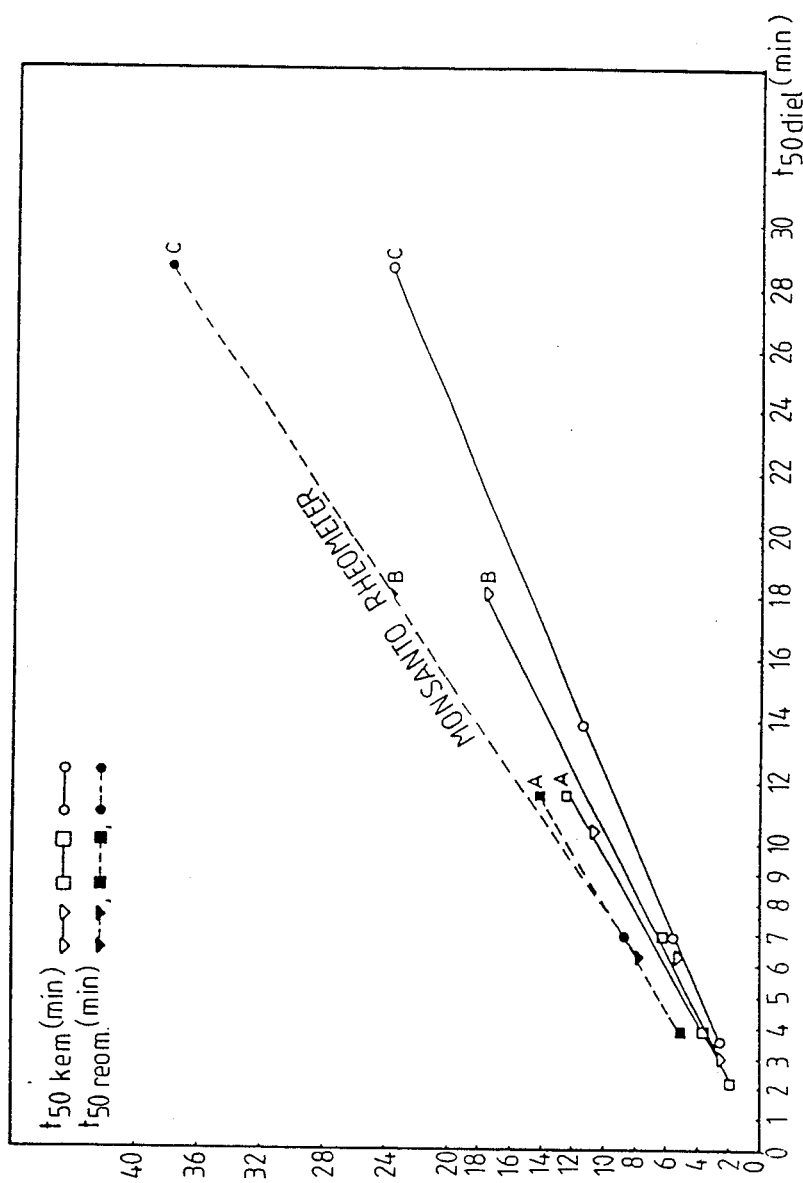

In addition to correctly indicating the start of the vulcanization the dielectric method has also been found to give valuable information about the degree of vulcanization. In FIG. 18 the times up to $t_{50}$, i.e. the time necessary to reach 50% of full vulcanization measured chemically, on one hand—$t_{50\ chem}$ (min)—and by the rheometer—$t_{50\ rheometer}$—, on the other hand have been plotted as a function of $t_{50\ diel}$.

In general it can be observed that the Monsanto rheometer gives longer $t_{50}$-times than the isothermally determined $t_{50\ chem}$ and $t_{50\ diel}$ times. These results agree well with those previously indicated in so far as the Monstanto rheometer gives longer vulcanization times than measuring methods operating under isothermal conditions.

Example 2 concerning natural rubber mixture D with EV-vulcanization systems.

As previously mentioned and as also apparent from the previous table, the conventional sulphur/accelerator system in mixture A has been exchanged for an accelerator/sulphur donor system in mixture D.

Figure 19:
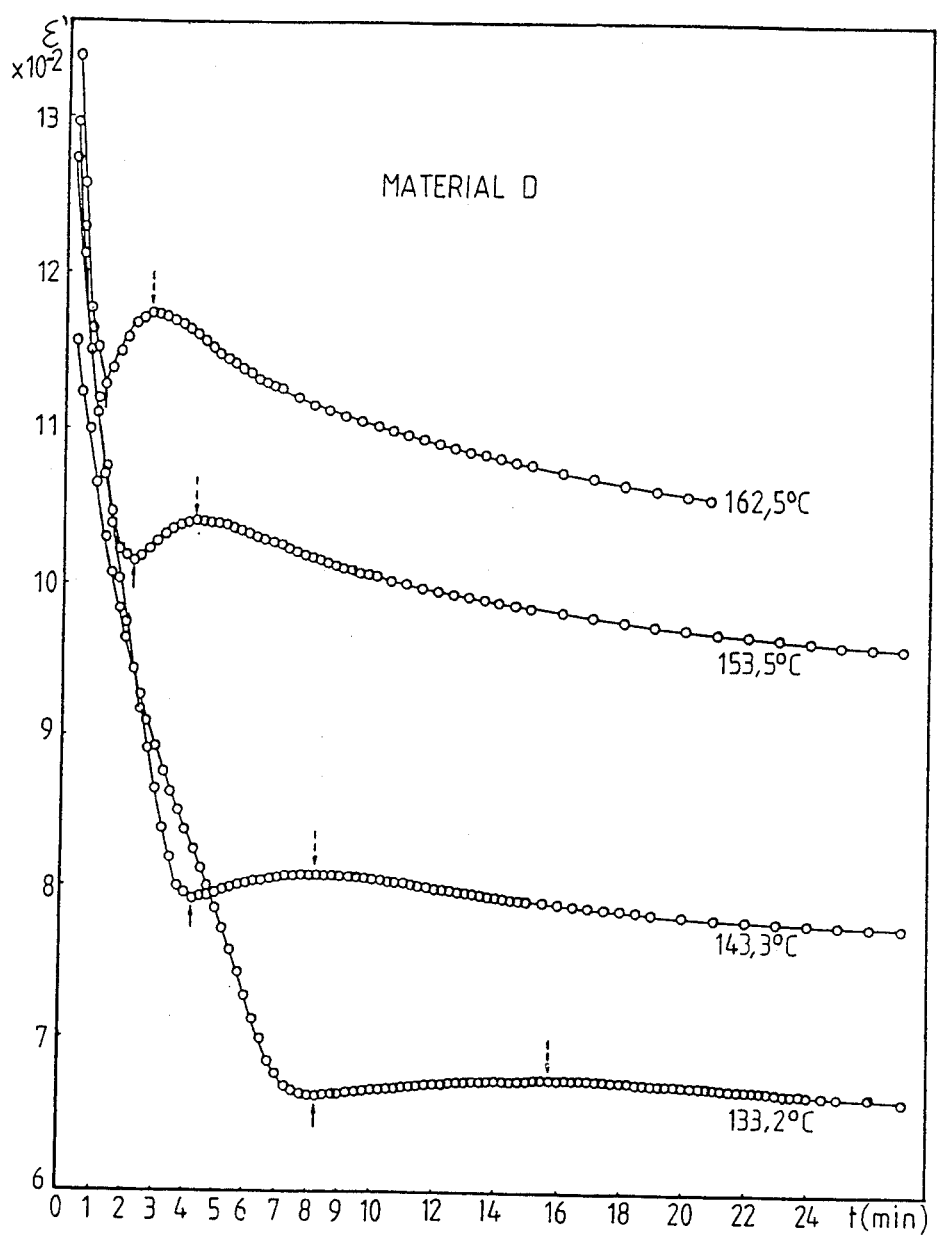

In FIG. 19 dielectric curograms for mixture D are shown taken at 300 kHz and about 130°, 140°, 150° and 160° C. $\epsilon'_r$ as a function of the time shows the same initial course as for the mixtures A, B and C, i.e. $\epsilon'_r$ first decreases. As distinguished from the mixtures A, B and C the curogram of mixture D has two inflection points marked by whole arrows ($\epsilon'_{r\ min}$) and dashed arrows ($\epsilon'_{r\ max}$) in FIG. 19.

Figure 20:
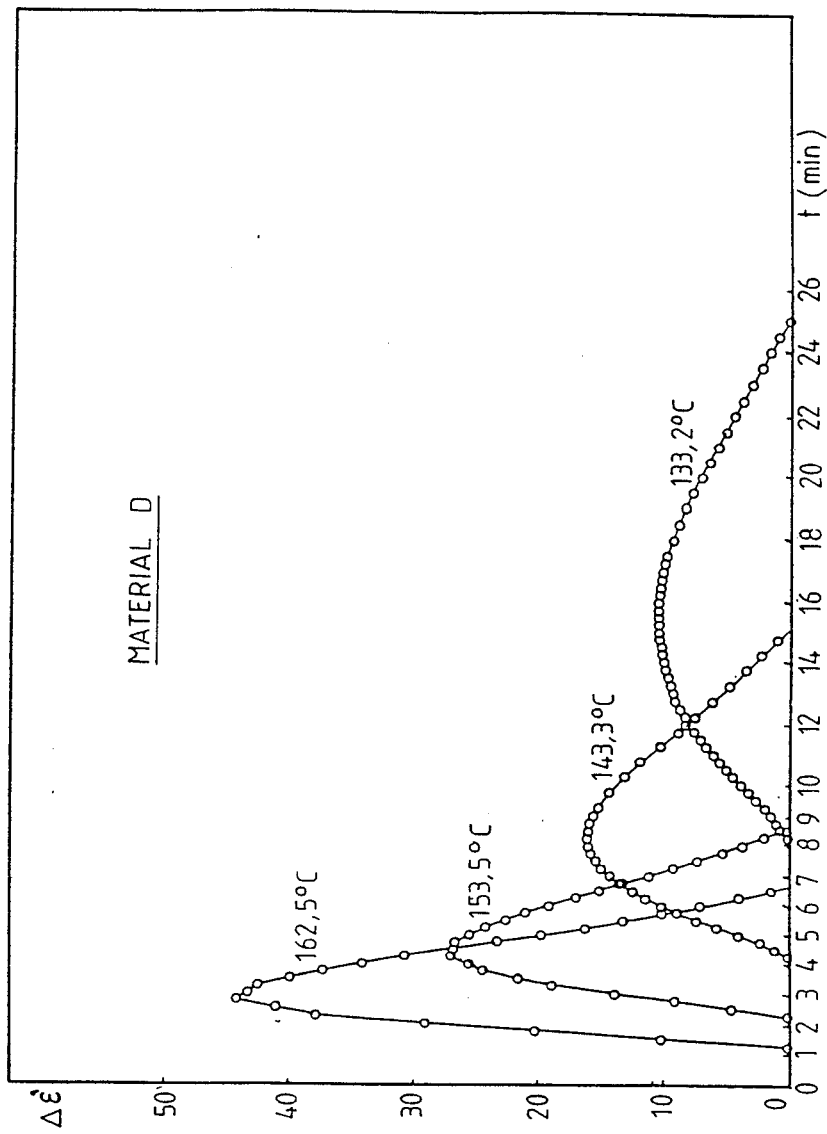

In FIG. 20 $\Delta\epsilon'_r$ is shown as a function of the vulcanization time. The inclination of the left sides of the loops and the maximum value of $\Delta\epsilon'_{r\ max}$ are increased when the vulcanization time is increased. The width of the loops increases when the vulcanization temperature is reduced.

Figure 21:
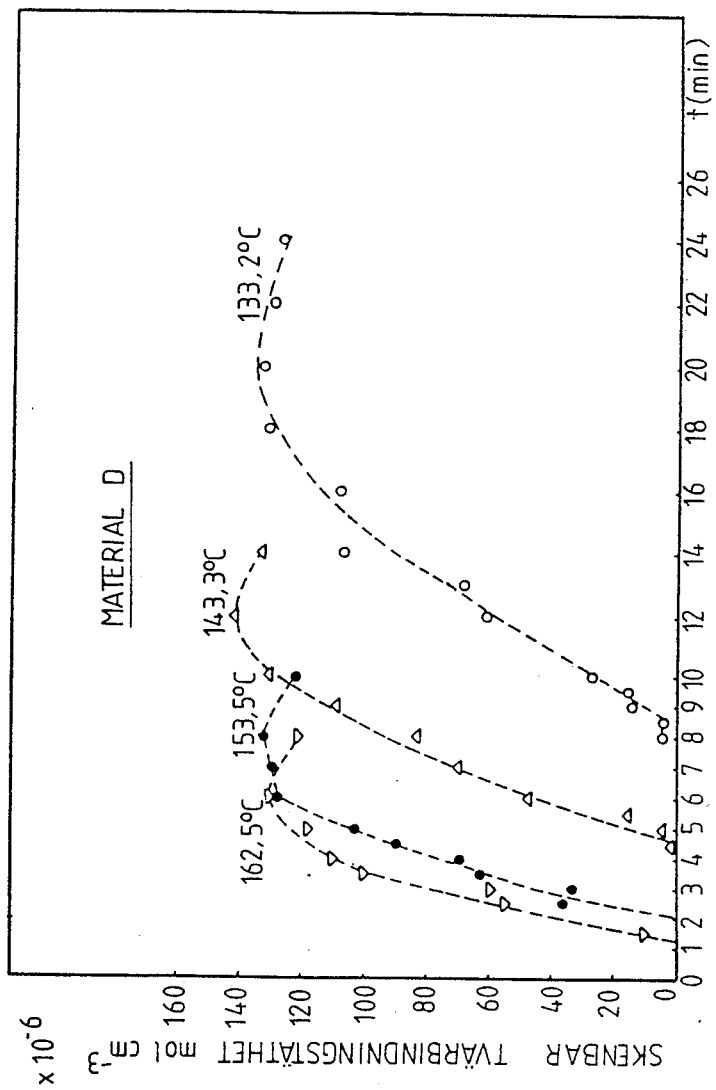

In FIG. 21 the chemically determined crosslinkage density of mixture D is shown as a function of vulcanization temperature and time. The maximum crosslinkage density at different vulcanization temperatures varies much less than for the mixtures A, B and C which is in good agreement with previously known results.

Figure 22:
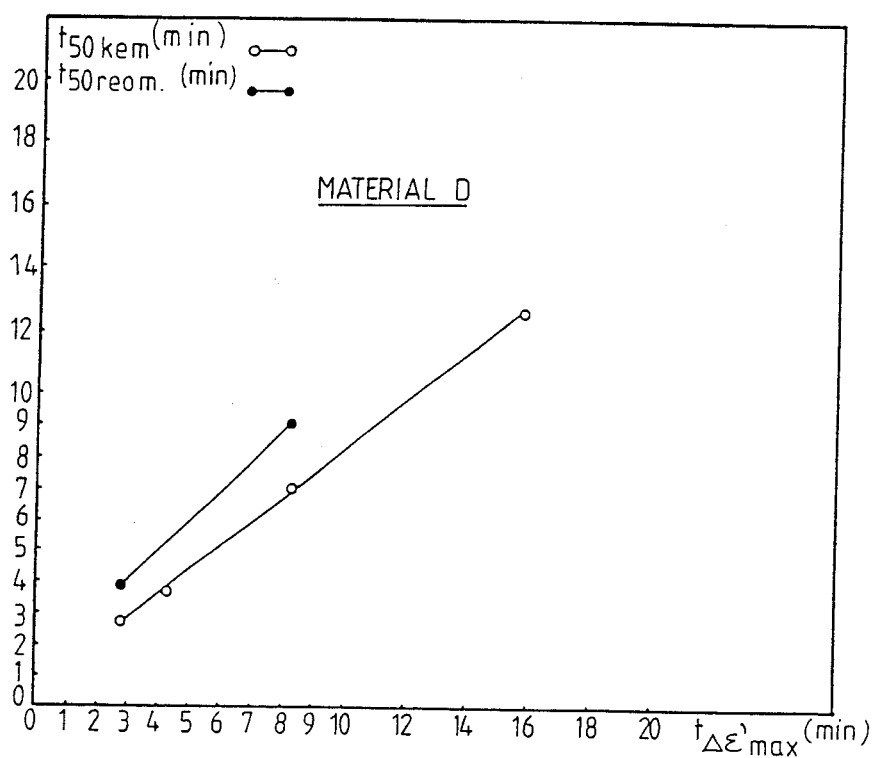

In FIG. 22 $t\Delta\epsilon'_{r\ max\ diel}$ (marked by dashed arrows in FIG. 19) has been plotted as a function of $t_{50\ chem}$ (min) and $t_{50}$ rheometer (min) in the same way as in FIG. 18.

It is apparent from FIGS. 19 and 21 that the vulcanization start $\epsilon'_{r\ min}$ (see also $\Delta\epsilon'_r=0$ in FIG. 20) well coincides with the vulcanization start determined chemically (FIG. 21) while $\epsilon'_{r\ max}$ is well correlated with $t_{50\ chem}$ (min) which has been plotted in FIG. 22 together with $t_{50\ rheometer}$ (min).

In the same way as for mixtures A, B and C the rheometer also gives longer vulcanization times for mixture D than for the isothermal methods.

Example 3 concerning mixtures F, G, H and I of natural rubber with conventional sulphur/accelerator systems and with a varying amount of sulphur.

If a measuring technique should be of any value for i.e. mixture development and/or routine testing of rubber mixtures the method should be able to detect not only big changes in the vulcanization characteristic exemplified by mixture A-D but also be able to detect small changes such as small variations in the sulphur content. In order to investigate the ability of the dielectric method to detect variations of rubber mixtures that might be designated as normal mixture to mixture variations which may arise under industrial conditions the mixtures shown in the following table 2 were investigated.

|  | F | G | H | I |
|---|---|---|---|---|
| SMR CV 60 | 100 | = | = | = |
| ISAF N220 | 45 | = | = | = |
| Dutrex 729 HP | 8 | = | = | = |
| ZnO | = | = | = | = |
| Stearic acid | 1 | = | = | = |
| TMQ | 1.5 | = | = | = |
| 6 PPD | 1.5 | = | = | = |
| Microcrystalline wax | 2 | = | = | = |
| CBS | 0,8 | = | = | = |
| Sulphur | 1.5 | 2.0 | 2.5 | 3.0 |

Concerning abbreviations, see table 1.

Figure 23:
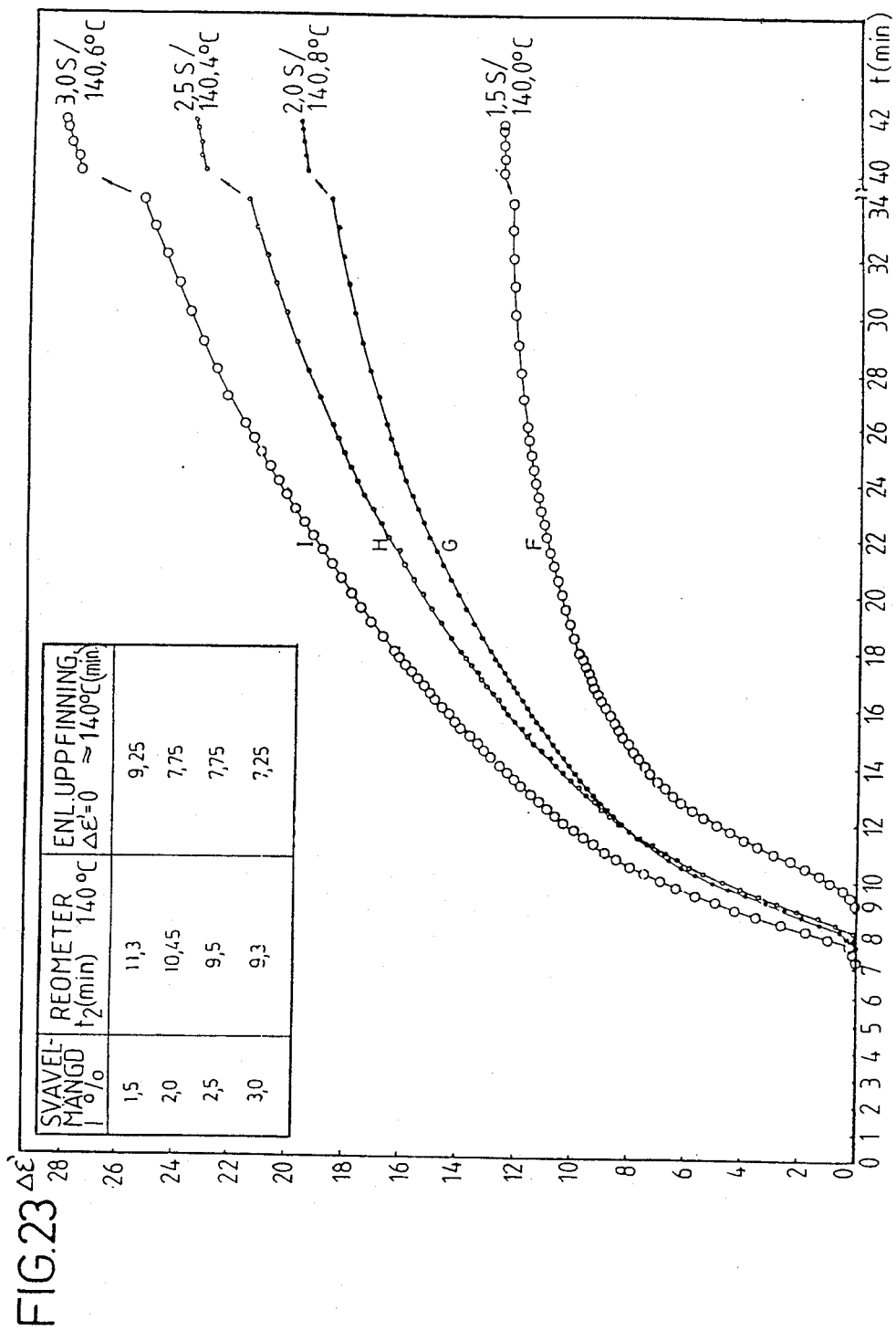
Figure 24:
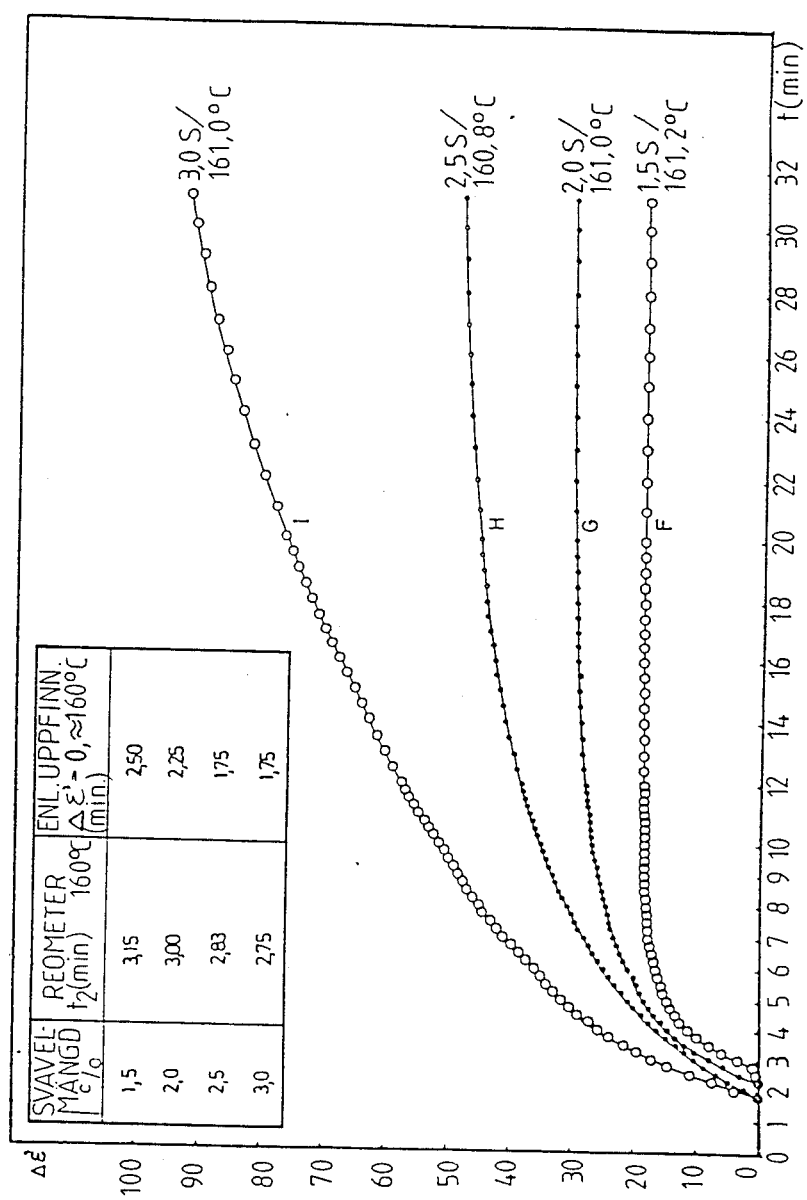

Dielectric curograms ($\Delta\epsilon'_r$ as a function of the time) for the mixtures F-I recorded at 300 kHz and the temperatures 140° and 160° C. are shown in FIGS. 23 and 24.

$\Delta\epsilon'_r$ as a function of the time has, as is expected, the same form as the curves previously reported in FIG. 11, i.e. $\Delta\epsilon'_r$ increases the whole time monotonously for the curograms recorded at 140° C. while $\Delta\epsilon'_r$ of the curograms recorded at 160° C. of the two lowermost sulphur contents (1.5 and 2.0 phr.S) reaches a constant $\Delta\epsilon'_r$ value more quickly the lower the sulphur content is.

As is apparent from FIGS. 23 and 24 $\Delta\epsilon'_r$ is very sensitive to the amount of sulphur in the mixture—more sensitive the higher the vulcanization temperature is.

The following general conclusions can be drawn from the dielectric curograms shown in FIGS. 23 and 24.

(a) An increased amount of sulphur and increased temperature will result in that $\Delta\epsilon'_r$ increases faster than if the sulphur content and the temperature are low. This agrees well with what is previously known about the network structure of the sulphur vulcanized natural rubber in the sense that high sulphur contents in combination with high vulcanization temperature generate a polar network which is reflected here in the form of increasing capacity.

(b) The start of vulcanization is detected quite correctly by means of the dielectric method as compared with the chemically determined crosslinkage densities of mixtures F and I shown in FIG. 25. When the sulphur content is reduced the start of the vulcanization is moved towards longer times which agrees well with the results obtained by means of the Monsanto Rheometer, however with the essential difference that the dielectric results, as a consequence of the completely isothermal conditions under which these are recorded, are displaced towards shorter times, which is apparent from the tables in FIGS. 23 and 24.

(c) The $\Delta\epsilon'_r$-curves reach constant values more quickly the lower the sulphur content is and the higher the temperature is, as is shown in FIGS. 23 and 24.

Dielectric vulcametry, i.e. in-situ measurements of how the dielectric properties of vulcanizing rubber are changed as a function of vulcanizing time and temperature has been found to give valuable information about the start of the vulcanization and the degree thereof. Dielectric vulcametry has turned out to be a powerful tool in mixture development because the method has a high sensitivity to minimal changes in the concentration of e.g. vulcanizing agent, accelerators and retardants.

Another advantage of the dielectric method as compared with previously known analysis techniques—mechanical rheometers—is that the amount of test material required per analysis is very small (less than 0.5 g) with the result that the analysis can be carried out under quite isothermal conditions because the test material can be heated to the predetermined temperature in less than one second.

Another advantage of the dielectric technique is that it opens the possibility of measuring the course of vulcanization directly in the vulcanized products by using the multi-channel electrode described in Swedish patent application 8501270-6.

The invention is not restricted to what has been described above and shown in the drawings but can be changed and modified in several different manners within the scope of the inventive thought defined in the claims.

I claim:

1. An apparatus for determination of basic values from a material specimen for analysis of the vulcanization characteristic of the material comprising:

two electrodes having plane-parallel sides facing each other which can be heated to temperatures in excess of 100° C.;

means for compressing a material specimen between said electrodes to form a body having a predetermined shape and thickness, said electrodes being intimately connected with the body after shaping and said electrodes forming a capacitor together with said body;

means connected to the electrodes for measuring a capacitance and a loss angle of the capacitor;

temperature sensing means connected to at least one of said electrodes for determining a temperature thereof; and means connected to said temperature determining means and said capacitance and loss angle measuring means, for recording the resulting values as said basic values.

2. The apparatus of claim 1 wherein the electrodes are supported by platens included in a press and galvanically separated from said platens.

3. The apparatus of claim 2 wherein the temperature sensing means comprises a thermoelement and a digital thermometer with analog output, said thermoelement being connected to one electrode and galvanically separated from said one electrode.

4. The apparatus of claim 3 further comprising a specimen carrier formed of an electrically non-conductive material and having plane-parallel sides, said specimen carrier being adapted to be located between said two electrodes and to enclose in a cavity of said form and thickness the material specimen during its shaping.

5. The apparatus of claim 4, wherein the platens of the press comprise heat plates for heating the electrodes and consequently specimen carrier and material specimen to the intended temperature, said heat plates being connected to a temperature regulator for adjusting the temperature.

6. The apparatus of claim 5 wherein the unit recording the basic values is a 3-pen writer.

7. A method of determining basic values from a material specimen for analysis of the vulcanization of the material, comprising the steps of:

placing the specimen between two electrodes, said two electrodes having planar sides parallel and facing each other;

bringing said planar sides into intimate contact with said specimen thereby forming a capacitor;

applying pressure and a temperature in excess of 100° C. to said specimen thereby shaping said specimen to a predetermined thickness;

measuring a capacitance and loss angle of the capacitor;

measuring the temperature of at least one of said two electrodes; and recording the capacitance, loss angle and temperature of said at least one of said two electrodes as said basic values.

8. A method as in claim 7 wherein the specimen is placed into the cavity in a specimen carrier prior to being placed between said two electrodes, said specimen carrier having to parallel sides and being composed of an electrically nonconductive material.

9. A method as in claim 8, wherein the specimen carrier is heated to the intended temperature before the specimen is placed in its cavity to be shaped.

10. A method as in claim 9 wherein said predetermined thickness is less than 0.25 mm.

11. A method as in claim 9 wherein said predetermined thickness is less than 1 mm.

12. The method as in claim 11 wherein the capacitance and loss angle are measured by means of an impedance analyzer and the temperature of the electrode plates is measured by means of a thermoelement connected to a digital thermometer with analog output.

* * * * *